(12) United States Patent
Manzella et al.

(10) Patent No.: US 10,424,023 B1
(45) Date of Patent: *Sep. 24, 2019

(54) SYSTEM AND METHOD OF DETERMINING AN INSURANCE PREMIUM QUOTE BASED ON HUMAN TELEMATIC DATA AND STRUCTURE RELATED TELEMATIC DATA

(71) Applicant: ALLSTATE INSURANCE COMPANY, Northbrook, IL (US)

(72) Inventors: Matthew James Manzella, Glen Ellyn, IL (US); Alinawaz Ismaili, Skokie, IL (US)

(73) Assignee: Allstate Insurance Company, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,661

(22) Filed: May 1, 2018

Related U.S. Application Data

(63) Continuation of application No. 14/507,703, filed on Oct. 6, 2014, now Pat. No. 9,984,418.

(51) Int. Cl.
| | |
|---|---|
| *G06Q 40/08* | (2012.01) |
| *G08B 25/00* | (2006.01) |
| *G08B 19/00* | (2006.01) |
| *A61B 5/00* | (2006.01) |
| *H04Q 9/14* | (2006.01) |

(52) U.S. Cl.
CPC ........... *G06Q 40/08* (2013.01); *A61B 5/0002* (2013.01); *G08B 19/00* (2013.01); *G08B 25/00* (2013.01); *H04Q 9/14* (2013.01)

(58) Field of Classification Search
CPC .... G06Q 40/08; G06F 19/3418; G08B 25/00; G08B 25/008; G08B 19/00; A61B 5/0002; A61B 5/0015; A61B 5/0022; A61B 5/02; H04Q 9/14; H04Q 2209/30
See application file for complete search history.

(56) References Cited

U.S. PATENT DOCUMENTS

| | | | |
|---|---|---|---|
| 7,113,090 B1* | 9/2006 | Saylor | G08B 13/19682 340/5.33 |
| 8,620,693 B1* | 12/2013 | Schumann, Jr. | G06Q 40/08 705/4 |
| 9,984,418 B1* | 5/2018 | Manzella | G06Q 40/08 |
| 9,996,882 B1* | 6/2018 | Manzella | G06Q 40/08 |
| 2008/0146892 A1* | 6/2008 | LeBoeuf | G16H 50/30 600/300 |
| 2010/0286490 A1* | 11/2010 | Koverzin | G06F 19/3418 600/301 |
| 2011/0161100 A1* | 6/2011 | Peak | G06Q 40/08 705/2 |
| 2012/0036038 A1* | 2/2012 | Farmer | G06Q 20/102 705/26.7 |

(Continued)

*Primary Examiner* — Andrew W Bee

(57) ABSTRACT

Systems and methods are disclosed herein for pricing an insurance premium based on analysis of various telematic data. The system includes a user with a wearable human telematic sensor providing telematic data about the wearer. Also, the system and method includes at least one building/environment telematic sensor configured to provide telematic data about the building and surrounding environment. The various telematic data is communicated and processed to provide an insurance quote to the user based upon analysis of the telematic data.

20 Claims, 7 Drawing Sheets

(56) References Cited

U.S. PATENT DOCUMENTS

| | | | | |
|---|---|---|---|---|
| 2012/0072240 A1* | 3/2012 | Grosso | ............... | G06Q 40/08 |
| | | | | 705/4 |
| 2013/0150686 A1* | 6/2013 | Fronterhouse | ...... | G06F 19/3418 |
| | | | | 600/323 |
| 2013/0321637 A1* | 12/2013 | Frank | ............... | H04N 5/33 |
| | | | | 348/152 |
| 2014/0135644 A1* | 5/2014 | Kim | ............... | A61B 5/6803 |
| | | | | 600/545 |
| 2014/0136242 A1* | 5/2014 | Weekes | ............... | G06Q 40/08 |
| | | | | 705/4 |
| 2014/0172467 A1* | 6/2014 | He | ............... | B60K 28/066 |
| | | | | 705/4 |
| 2014/0257867 A1* | 9/2014 | Gay | ............... | G07C 5/00 |
| | | | | 705/4 |
| 2014/0306833 A1* | 10/2014 | Ricci | ............... | B60Q 1/00 |
| | | | | 340/901 |
| 2014/0358592 A1* | 12/2014 | Wedig | ............... | G06Q 40/08 |
| | | | | 705/4 |
| 2015/0025917 A1* | 1/2015 | Stempora | ............... | G06Q 40/08 |
| | | | | 705/4 |
| 2015/0061859 A1* | 3/2015 | Matsuoka | ............... | G08B 27/00 |
| | | | | 340/501 |
| 2015/0221196 A1* | 8/2015 | Rafin | ............... | G06F 19/3418 |
| | | | | 340/521 |
| 2015/0287310 A1* | 10/2015 | Deliuliis | ............... | H04W 4/90 |
| | | | | 340/628 |
| 2017/0109829 A1* | 4/2017 | Amigo | ............... | G06Q 40/08 |

* cited by examiner

500

600

700

US 10,424,023 B1

SYSTEM AND METHOD OF DETERMINING AN INSURANCE PREMIUM QUOTE BASED ON HUMAN TELEMATIC DATA AND STRUCTURE RELATED TELEMATIC DATA

CROSS-REFERENCE TO RELATED APPLICATION

This application is a continuation of U.S. patent application Ser. No. 14/507,703, filed Oct. 6, 2014, and titled: System and Method for Determining an Insurance Premium Quote Based on Human Telematic Data and Structure Related Telematic Data

FIELD OF THE INVENTION

In general, the invention relates to a computerized system and method for determining the price of an insurance premium based on human telematic data and building or structure telematic data.

BACKGROUND

The use of telematics sensors and other location-aware, status-aware devices have begun to make their way into the marketplace. Currently, they are used with vehicles to determine a driver's speed or perhaps location/route traveled. This information is typically used to ensure employees are not deviating from established travel routes or driving in an unsafe fashion. The data received is currently data depicting how or where a person has driven. It is inherently dated or otherwise depicting past events when viewed or analyzed. As the current systems and methods are not set up to provide real time analysis of an individual or their current environment, the systems cannot provide a user with information regarding near real time data with regards to driving activity and health status. Current systems are basing insurance premium quotes on outdated data or incomplete data.

As such, what is needed is a system and method that monitors, near real time, a user and their environment that is capable of providing a more accurate analysis and insurance premium quote.

SUMMARY

A system for processing building environmental safety status health data and building data related to the determination of an insurance quote for a user. The system includes a communications interface configured to receive health telematics data collected by a telematics data acquisition device. The telematics data acquisition device is configured to collect health telematic data of a building environmental safety status, the health telematic data being indicative of the building environmental safety status health while the user is within a building. Additionally, the data acquisition device is also configured to receive building telematic data collected by a telematics data acquisition device, wherein the telematics data acquisition device is configured to collect telematics data of a building indicative of building safety. The device provides the health telematic and the building telematic data to a business logic processor for the development of an insurance premium quote based on at least one of the received health telematics data or building telematic data. Further, the system transmits the insurance quote to the user.

An additional aspect includes a method of providing an insurance premium quote to a user based upon human telematic data and building telematic data. The method includes providing a first sensor to be worn by a user and a first sensor data indicative of measured at least one user health telematic data. Further, the method includes providing a second sensor, in communication with a building being occupied by the user, the second sensor outputting a second sensor data indicative of a measured at least one building telematic data. Still further, the method includes providing a computing unit, in communication with the first sensor and the second sensor, the computing unit storing program instructions for execution by the computing unit. The computing unit receives the first sensor data and the second sensor data, calculates a risk level associated with the first sensor data and the second sensor data and, provides an output insurance premium quote indicative of the risk level of first sensor data and the second sensor data to the user.

DETAILED DESCRIPTION

To provide an overall understanding of the invention, certain illustrative embodiments will now be described, including systems and methods for monitoring individual telematic data, such as, individual health status while simultaneously monitoring building/user environment telematic data, and pricing an insurance premium based on the monitored telematics data. This system and method is also used to provide a feedback to the user based upon the monitored user and building/environmental telematic data. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1:
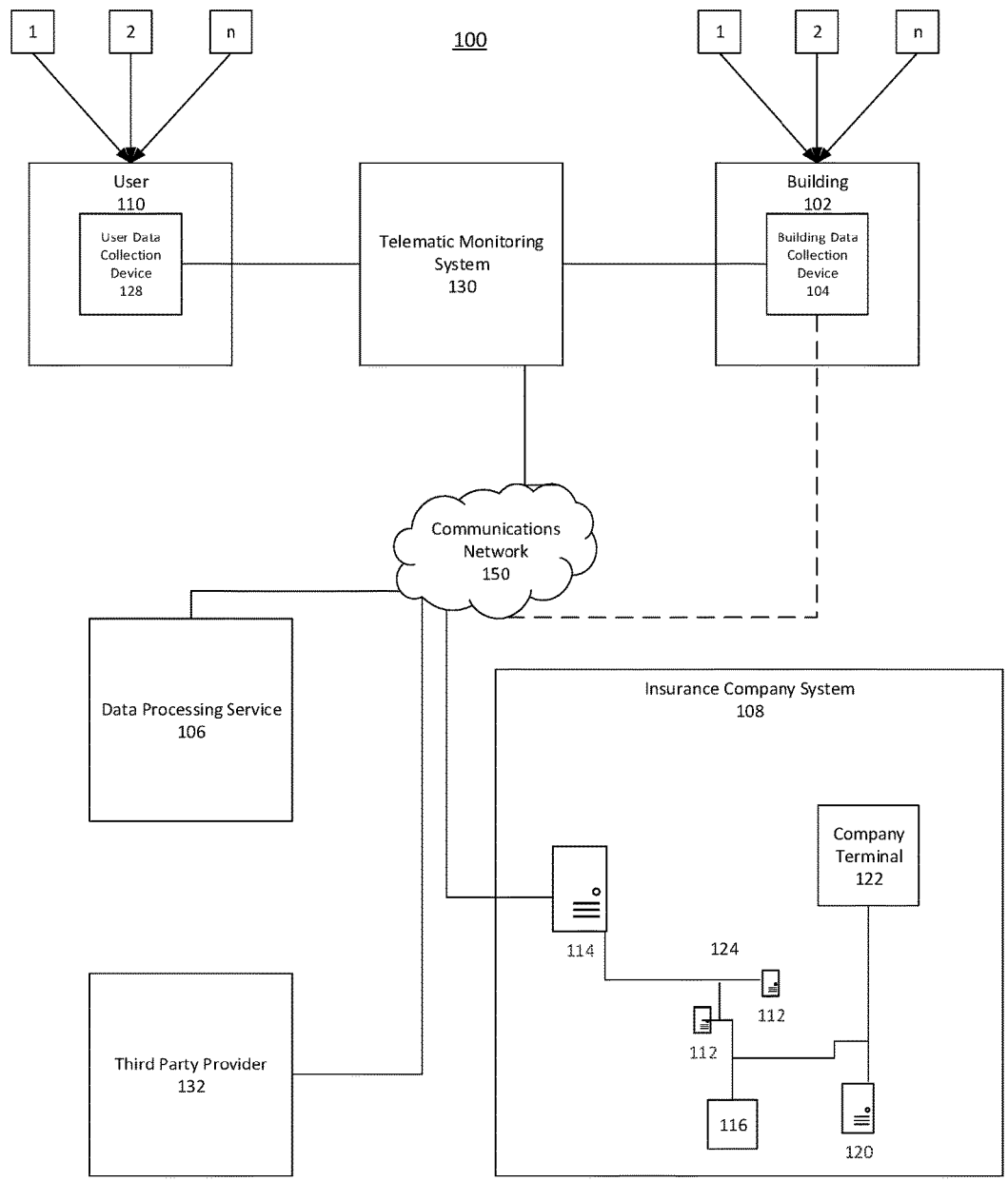
FIG. 1 is an architectural model of a system for producing an insurance premium quote, according to an illustrative embodiment of the invention.

FIG. 1 is a block diagram of a system 100 for monitoring individual health status, building/user environment status, and pricing an insurance premium, according to an illustrative embodiment. The system 100 uses telematic data to determine the behavior and safety of a building/user environment status, and its user/occupier. An insurance company uses data related to building/user environment structural condition, building/user environment air quality, geographic location, temperature/humidity level, HVAC status, security devices, ingress/egress configuration, building materials, nature of use (current/historic), surrounding environmental conditions, etc., to assess the behavior and safety of the user. Additionally, the insurance company uses data related to individual health measurements, and user environmental measurements to further assess the behavior and safety of the user. With a sufficient amount of data, the insurance company can calculate an insurance premium for the user based on user health measurements, user environmental measurements, and the condition of the building/user environment. In some implementations, the telematics data is processed or assessed by a third party data processing service. In addition, the insurance premium price may be set by an underwriter, who may be a part of the insurance company or otherwise affiliated with or in a third party arrangement with the insurance company.

The system includes a user 110 having at least one user data collection device 128 in communication with the user 110. The user data collection device 128 is configured to measure any variety of user health status measurements such as, without limitation body mass index, blood pressure, respiratory rate, heart rate, perspiration, body temperature, eye dialation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants, etc. Suitable exemplary sensing equipment includes wearable devices like Nike's Fuelband™ or a similar activity tracking sensor such as Fitbit™. Still further, Netatamu's June™ and Sunsprite™ by GoodLux Technology are suitable non limiting examples of personal sun exposure detectors. By way of further non limiting example, is a personal air pollution sensor by Carnegie Mellon under the name Airbot™. Likewise, there are a variety of smart clothing options available that include imbedded sensors for health monitoring. Further, wearable EEG sensors are also known, as are blood glucose level sensors, and transdermal sensors for determination of alcohol consumption. Alternatively or additionally, the user data collection device 128 may be configured to sense environmental factors around the user 110. In this manner, it can be determined if the user 110 has entered or is in an unsafe area. Suitable non limiting examples of such user data collection device 128 include oxygen sensors, carbon monoxide sensors, methane sensors, pollution sensors, radiation sensors. All such user data collection devices 128 are capable of transmitting data via a network or direct wire.

The system 100 also includes one or more buildings 102, each having a building data collection device 104. For the purposes of this disclosure, a "building 102" is defined as any static or semi static structure/environment that a user may spend time in or pass through. By way of non-limiting example, the building 102 may be a home, apartment, condo, office, tent, hangar, store, industrial or commercial structure, rail system, bridge, tunnel, mine/cave, or any other building/structure that may be interacted with, at least temporarily, by a user. A building data collection device 104 is coupled to a building 102 for collecting data about the building's location, or other information that can be used to determine building safety. The building data collection device 104 may be positioned inside the building, attached to the outside of the building, or integrated into the building. For buildings with multiple users, the data may be associated with the building itself or with the individual users.

In some embodiments, data from the user data collection device 128 and/or the building data collection device 104 is directly transmitted to the insurance company system 108 and/or telematic monitoring system 130 without traveling through the communications network 150. In other embodiments, the user data collection device 128 and/or the building data collection device 104 is in communication with an insurance company system 108 and/or a telematic monitoring system 130 over a communications network 150. The user data collection device 128 and/or the building data collection device 104 may communicate with the insurance company system 108 though a wireless network such as a cellular network or by using a wireless Internet connection.

The user data collection device 128 and/or building data collection device 104 can be any computing device or plurality of computing devices in cooperation having a data collection sensor (e.g., an antenna or a seismograph), a processor, a memory, and a means for transmitting the collected data. The building 102 or building data collection device 104 may include an antenna for receiving signals from global navigation satellite system (GNSS) satellites, numbered 1 through n in FIG. 1. In some embodiments, the user data collection device 128 and/or building data collection device 104 is also configured to process the collected data, e.g., by summarizing and/or compressing the data. In some embodiments, the data processing protects the user's privacy by encrypting the data, removing location information, producing summary information, or taking other measures to reduce the likelihood that location information or other sensitive information are received by the insurance company or third parties. The components of the building data collection device 104 are discussed further in relation to FIG. 3, and an alternative data collection device is described in relation to FIG. 4. It will be understood that a similar configuration may be used with the user data collection device 128

In some embodiments, rather than sending collected data directly to the insurance company system 108, the user data collection device 128 and/or building data collection device 104 or the telematic monitoring system 130 sends collected data to a data processing service 106, which processes the data to determine user safety and building safety information that is then sent to the insurance company system 108 for setting an insurance premium price. This can help protect a user's privacy, since the insurance company does not receive detailed data about a user's location, but only receives summary information, e.g., a building or environmental/safety rating or score. Using a data processing service 106 in some implementations also preferable to having the user data collection device 128 and/or building data collection device 104 process data because it reduces the processing power needed by the user data collection device 128 and/or building data collection device 104 and because using a third party data processing service 106 may also make it more difficult to tamper with the data. The data processing service can perform additional monitoring functions, such as building security monitoring or providing location-based alerts (e.g., alerting a parent or employer when a building sensor is activated) and safety alerts. Additionally, or to the contrary, if a potentially dangerous condition is determined, warning messages may be sent to the user 110.

The insurance company system 108 includes a plurality of application servers 112, a plurality of load balancing proxy servers 114, an insurance company database 116, a processing unit 120, and company terminal 122. These computing devices are connected by a local area network 124.

The application servers 112 are responsible for interacting with the user data collection device 128 and/or building data collection device 104 and/or the data processing service 106. The data exchange between the insurance company system 108 and telematic monitoring system 130, the user data collection device 128 and/or building data collection device 104, and/or data processing service 106 can utilize push and pull technologies where the application servers 112 of the insurance company system 108 can act as both a server and client for pushing data to the telematic monitoring system 130, the user data collection device 128 and/or building data collection device 104, and/or data processing service 106 (e.g., which buildings to monitor, when to stop data collection, rules for monitoring services requested by the customer) and for pulling data from the telematic monitoring system 130, the user data collection device 128 and/or building data collection device 104, and/or data processing service 106. The application servers 112 or other servers of the insurance company system 108 can request to receive periodic data feeds from the telematic monitoring system 130, the user data collection device 128 and/or building data collection device 104, or data processing service 106. The communication between the application servers 112 and the telematic monitoring system 130, the user data collection device 128 and/or building data collection device 104, and/or data processing service 106 can follow various known communication protocols, such as TCP/IP. Alternatively, the application servers 112 and telematic monitoring system 130, the user data collection device 128 and/or building data collection device 104, and/or data processing service 106 can communicate with each other wirelessly, e.g., via cellular communication, Wi-Fi, Wi-Max, or other wireless communications technologies or combination of wired or wireless channels. The load balancing proxy servers 114 operate to distribute the load among application servers 112.

The insurance company database 116 stores information about insurance policies. For each insurance policy, the database 116 includes for example and without limitation, the following data fields: policy coverage, policy limits, deductibles, the agent responsible for the sale or renewal, the date of purchase, dates of subsequent renewals, product and price of product sold, applicable automation services (for example, electronic billing, automatic electronic funds transfers, centralized customer service plan selections, etc.), customer information, customer user behavior, customer payment history, or derivations thereof.

The processing unit 120 is configured for determining the price of an insurance premium based on user behavior and other information related to the user and the building/building environment. The processing unit 120 may comprise multiple separate processors, such as a user behavior processor, which analyzes user behavior from raw or processed data received from the telematic monitoring system 130, the user data collection device 128 and/or building data collection device 104, and/or data processing service 106 over the communications network 150; and a business logic processor, which determines a premium price for a policyholder based on, among other things, user health state, user environment state and the user behavior. In some embodiments, insurance premium prices or information for making insurance pricing determinations may be generated by a third-party underwriter, which is separate from the insurance company system 108. An exemplary implementation of a computing device for use in the processing unit 120 is discussed in greater detail in relation to FIG. 2.

The company terminals 122 provide various user interfaces to insurance company employees to interact with the processing system 120. The interfaces include, without limitation, interfaces to review building/building environment data; to review building data; to review customer or potential customer measured health data; to retrieve data related to insurance policies; to manually adjust user behavior ratings; and to manually adjust premium pricing. In some instances, different users may be given different access privileges. For example, marketing employees may only be able to retrieve information on insurance policies but not make any changes to data. Such interfaces may be integrated into one or more websites for managing the insurance company system 108 presented by the application servers 112, or they may be integrated into thin or thick software clients or stand alone software. The company terminals 122 can be any computing devices suitable for carrying out the processes described above, including personal computers, laptop computers, tablet computers, smartphones, servers, and other computing devices.

User terminals can provides various user interfaces to customers to interact with the insurance company system 108 over the communications network 150. Customers may also use their personal computers, smartphones, tablet computers, or other computing devices as terminals for accessing user interfaces provided by the insurance company. For example, customers can access a web page or application provided by the insurance company to enter information pertaining to changes in their insurance policy, e.g., changes in policy coverage, addition or subtraction of users, addition or subtraction of buildings, relocation, addition or subtraction of various user sensors 128, etc.

In some embodiments, the user data collection device 128 and/or building data collection device 104 is/are not continually connected to the insurance company system 108 via the network 150. For example, the user data collection device 128 and/or building data collection device 104 may be configured to temporarily store data if the user data collection device 128 and/or building data collection device 104 becomes disconnected from the network, like when it travels out of range of cellular towers. When the connection is restored, the user data collection device 128 and/or building data collection device 104 can then transmit the temporarily stored data to the insurance company system 108. The user data collection device 128 and/or building data collection device 104 may alternatively be configured to connect to the communications network 150 through a user's home Wi-Fi network. In this case, the user data collection device 128 and/or building data collection device 104 stores all sensed data until it returns to the vicinity of the user's home, connects to the user's wireless network, and sends the data.

In some embodiments, data from a third party data provider 132 is accessed by one or more of the user data collection device 128 and/or building data collection device 104, the data processing service 106, the insurance company system 108, and/or the telematic monitoring system 130 over the communications network 150. Data from a third party data provider 132 can be used in calculating an insurance premium. For example, the third party data provider 132 can provide geologic/seismic or weather data that is processed in conjunction with the received telematics data to evaluate user behavior in view of the environmental/building conditions. Other third party data providers 132 provide data related to a customer or a potential customer, such as the customer's health record or credit history.

Figure 2:
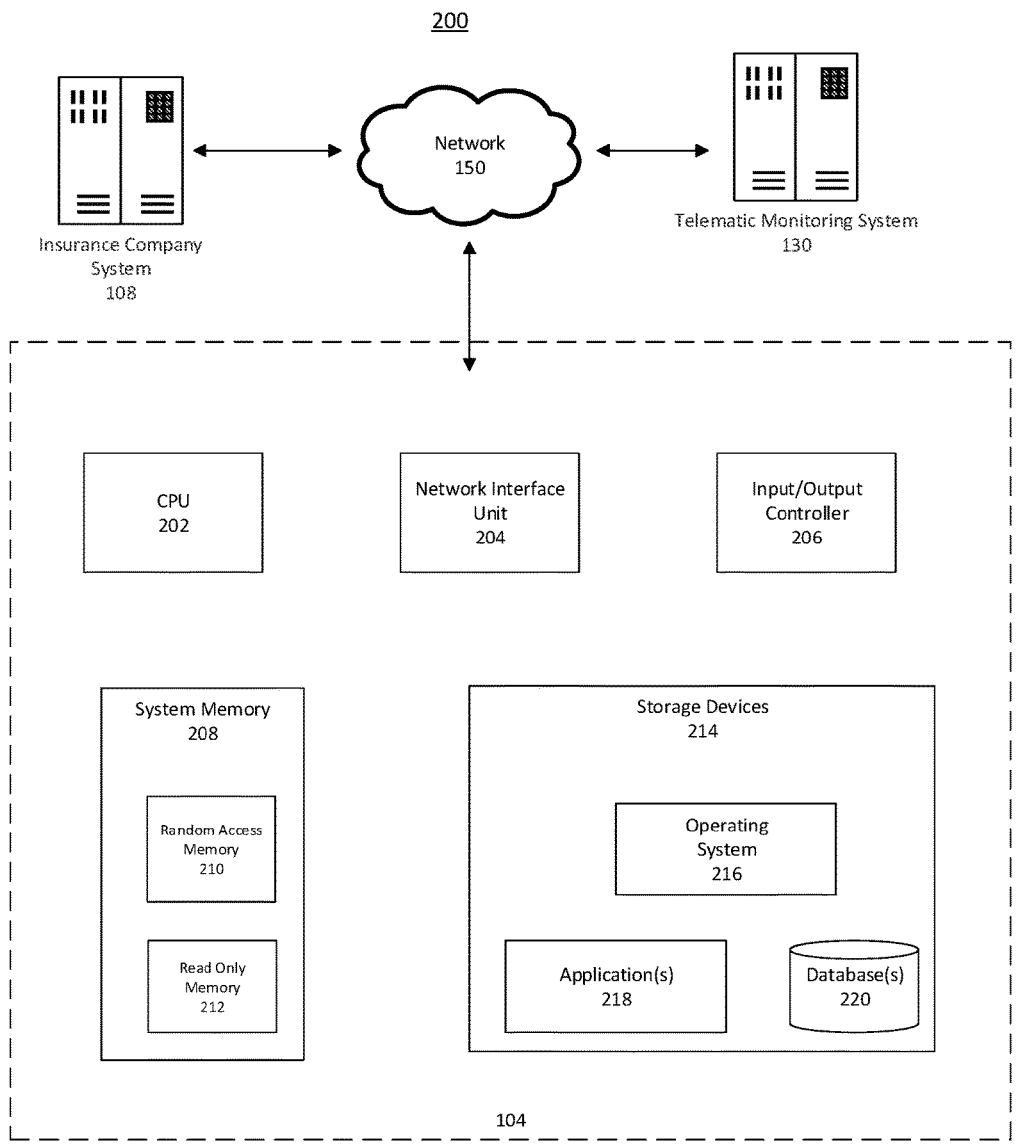
FIG. 2 is a block diagram of a computing system as used in FIG. 1, according to an illustrative embodiment of the invention.

FIG. 2 is a block diagram of a computing device 200 used for carrying out at least one of user health and/or behavior processing and business logic processing described in relation to FIG. 1, according to an illustrative embodiment of the invention. The computing device comprises at least one network interface unit 204, an input/output controller 206, system memory 208, and one or more data storage devices 214. The system memory 208 includes at least one random access memory (RAM) 210 and at least one read-only memory (ROM) 212. All of these elements are in communication with a central processing unit (CPU) 202 to facilitate the operation of the computing device 200. The computing device 200 may be configured in many different ways. For example, the computing device 200 may be a conventional standalone computer or alternatively, the functions of computing device 200 may be distributed across multiple computer systems and architectures. The computing device 200 may be configured to perform some or all of the user behavior and business logic processing, or these functions may be distributed across multiple computer systems and architectures. In the embodiment shown in FIG. 1, the computing device 200 is linked, via network 150 or local network 124 (also described in FIG. 1), to other servers or systems housed by the insurance company system 108, such as the load balancing server 114, and the application servers 112, and to the telematic monitoring system 130.

The computing device 200 may be configured in a distributed architecture, wherein databases and processors are housed in separate units or locations. The computing device 200 may also be implemented as a server located either on site near the insurance company system 108, or it may be accessed remotely by the insurance company system 108. Some such units perform primary processing functions and contain at a minimum a general controller or a processor 202 and a system memory 208. In such an embodiment, each of these units is attached via the network interface unit 204 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 202 comprises a processor, such as one or more conventional microprocessors and one or more supplementary co-processors such as math co-processors for offloading workload from the CPU 202. The CPU 202 is in communication with the network interface unit 204 and the input/output controller 206, through which the CPU 202 communicates with other devices such as other servers, user terminals, or devices. The network interface unit 204 and/or the input/output controller 206 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 202 is also in communication with the data storage device 214. The data storage device 214 may comprise an appropriate combination of magnetic, optical and/or semiconductor memory, and may include, for example, RAM, ROM, flash drive, an optical disc such as a compact disc and/or a hard disk or drive. The CPU 202 and the data storage device 214 each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 202 may be connected to the data storage device 214 via the network interface unit 204.

The CPU 202 may be configured to perform one or more particular processing functions. For example, the computing device 200 may be configured for calculating ratings related to user behavior. The same computing device 200 or another similar computing device may be configured for calculating an insurance premium for a building based at least upon one user behavior.

The data storage device 214 may store, for example, (i) an operating system 216 for the computing device 200; (ii) one or more applications 218 (e.g., computer program code and/or a computer program product) adapted to direct the CPU 202 in accordance with the present invention, and particularly in accordance with the processes described in detail with regard to the CPU 202; and/or (iii) database(s) 220 adapted to store information that may be utilized to store information required by the program. The database(s) 220 may include all or a subset of data stored in insurance company database 116, described above with respect to FIG. 1, as well as additional data, such as formulas or manual adjustments, used in establishing the insurance risk for a building.

The operating system 216 and/or applications 218 may be stored, for example, in a compressed, an uncompiled and/or an encrypted format, and may include computer program code. The instructions of the program may be read into a main memory of the processor from a computer-readable medium other than the data storage device 214, such as from the ROM 212 or from the RAM 210. While execution of sequences of instructions in the program causes the CPU 202 to perform the process steps described herein, hard-wired circuitry may be used in place of, or in combination with, software instructions for implementation of the processes of the present invention. Thus, embodiments of the present invention are not limited to any specific combination of hardware and software.

Figure 5:
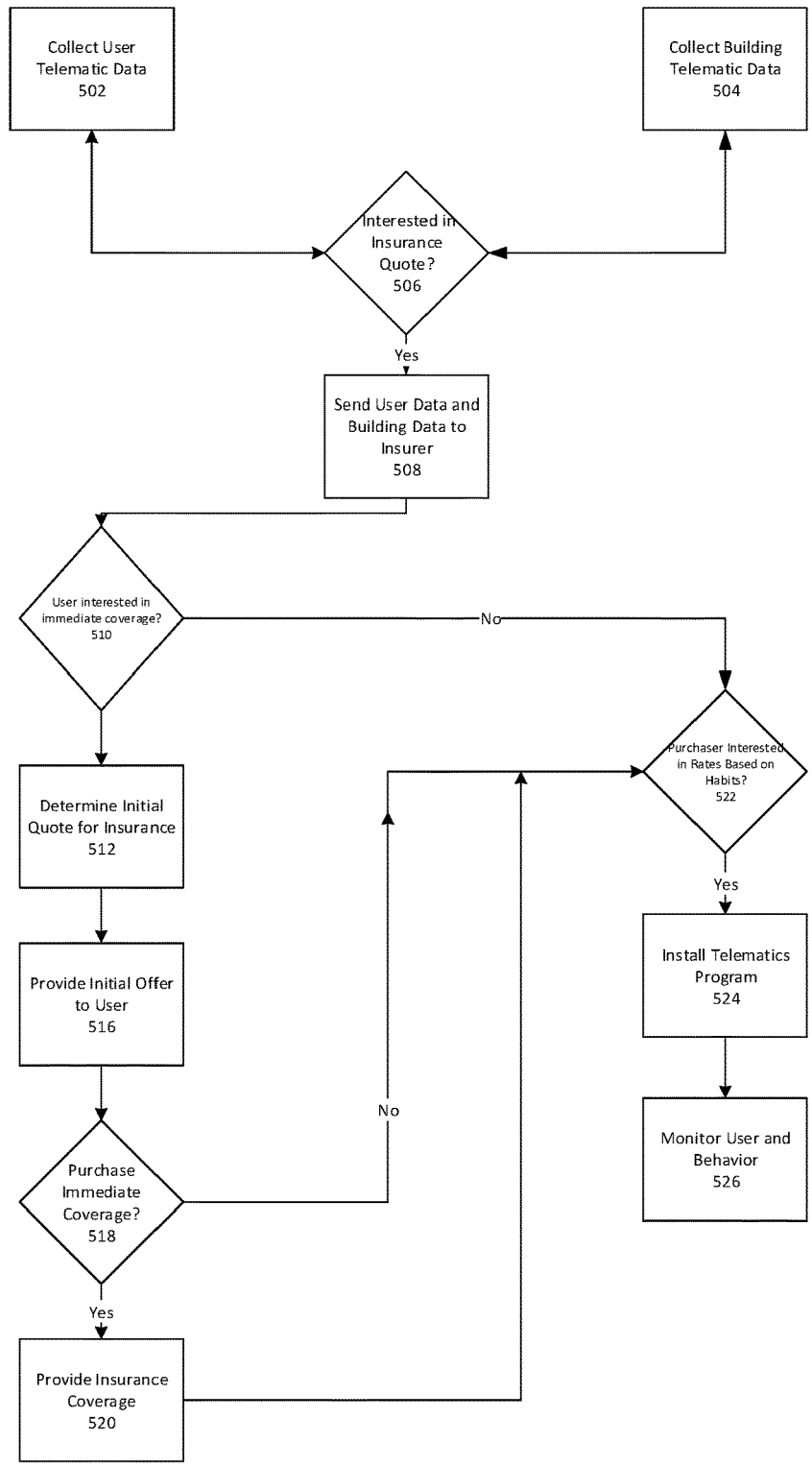
FIG. 5 is a flowchart of a method for determining an insurance quote for a user based on telematics data, according to an illustrative embodiment of the invention.
Figure 6:
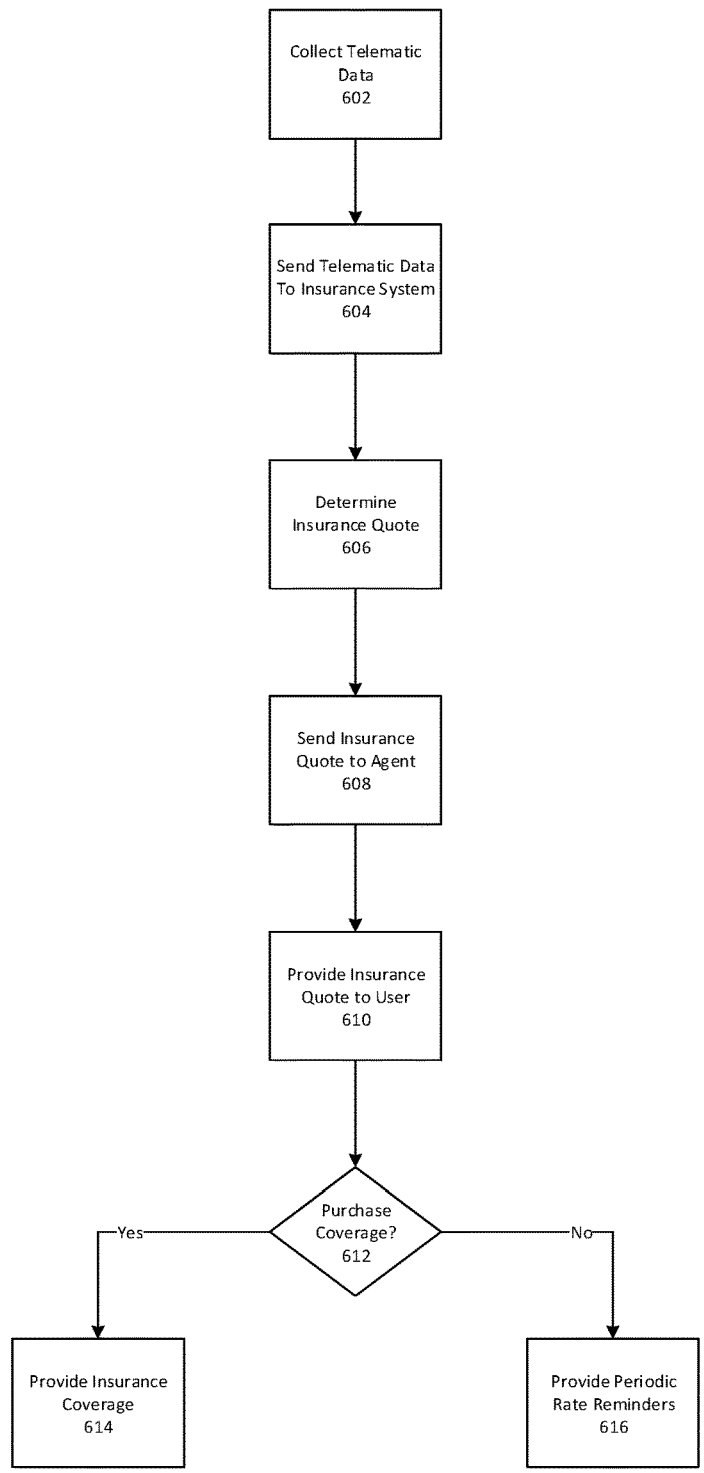
FIG. 6 is a flowchart of a method for determining an insurance quote for a user based on telematics data, according to an illustrative embodiment of the invention.
Figure 7:
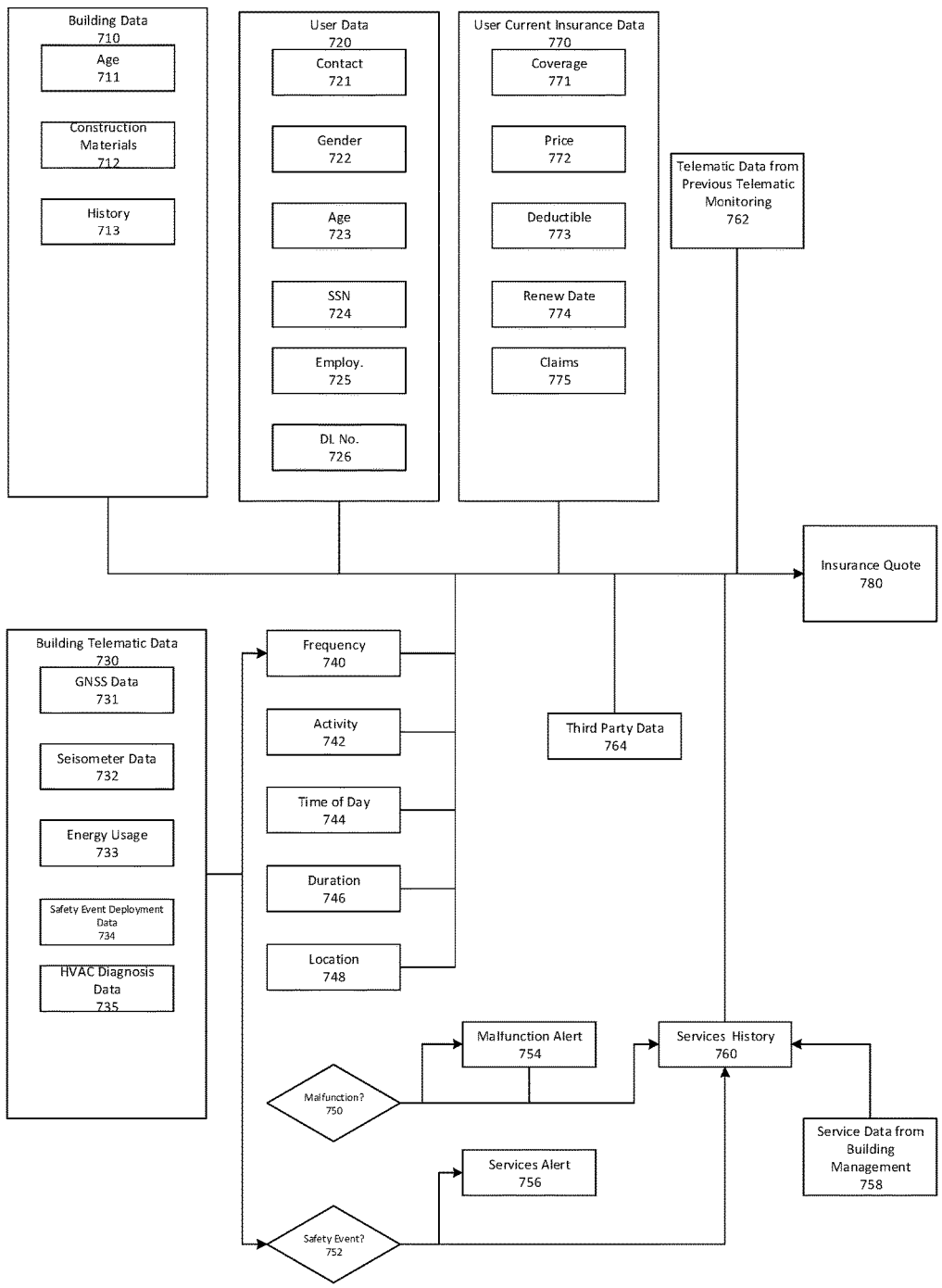
FIG. 7 is a data flow diagram illustrating a method for computing an insurance premium quote based on building telematics data, building data, user data, user telematic data, and service data, according to an illustrative embodiment of the invention.

Suitable computer program code may be provided for analyzing user behavior and determining an insurance premium price as described in relation to FIGS. 5 through 7. The program also may include program elements such as an operating system, a database management system and "device drivers" that allow the processor to interface with computer peripheral devices (e.g., a video display, a keyboard, a computer mouse, etc.) via the input/output controller 206.

The term "computer-readable medium" as used herein refers to any non-transitory medium that provides or participates in providing instructions to the processor of the computing device (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 202 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 3:
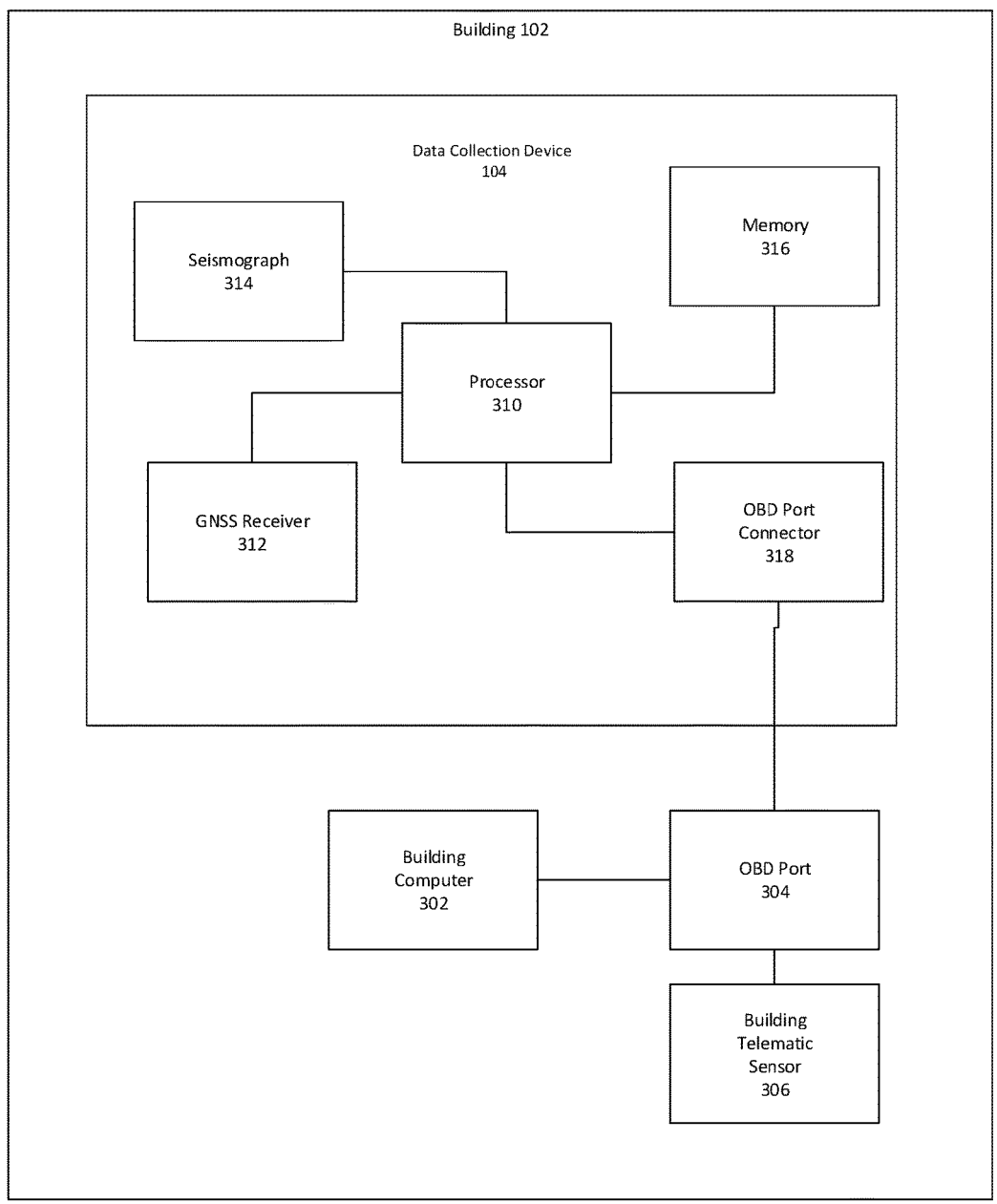
FIG. 3 is a block diagram of a building or static environment and a device coupled to the building or static environment for collecting data used for producing an insurance premium quote, according to an illustrative embodiment of the invention.

FIG. 3 is a block diagram of a building 102 having a building data collection device 104. As described in relation to FIG. 1, the building 102 may be a home, apartment, condo, office, tent, hangar, store, industrial or commercial structure, railway, roadway, sidewalk, bridge, tunnel, mine, or any other building/structure that may be occupied by a user. The building 102 includes a building computer 302, a diagnostics (OBD) port 304, and building telematics sensors 306. The building data collection device 104 is connected to the building 102 via a BD port connector 318 connected to the OBD port 304 to receive telematics data and other information. The building data collection device 104 includes a processor 310, a GNSS receiver 312, a seismograph 314, and memory 316. The building data collection device 104, may also include any other know sensing devices, such as, without limitation, gas sensors, heat sensors, fire sensors, water sensors (not shown). The processor 310 can be a CPU, a microprocessor, an FPGA, or any other processing unit that can be configured to execute a software or firmware program for telematics data acquisition. The processor 310 is in communication with the other elements of the building data collection device 104 to facilitate the operations of the building data collection device 104. The processor can also be configured to process data received from the GNSS receiver 312, the seismograph 314, and the BD port connector 318. Data processing may include analyzing user behavior, determining if service is needed, determining if there is an unsafe status with the building, formatting data, or encrypting data.

The GNSS receiver 312 includes an antenna and associated signal processing circuitry for receiving signals from global navigation satellite system (GNSS) satellites, such as the satellites numbered 1 through n in FIG. 1, and determining its location from the signals. GNSS satellites may be, for example, GPS, GLONASS, Galileo, or Beidou satellites which send time and orbital data from which the building data collection device 104 can calculate its location. In some configurations, the processor 310 calculates the location of the user from data from the receiver 312. The processor 310 can pull location data from the GNSS receiver 312 at set time intervals, such as every 0.1 seconds, 0.2 seconds, 0.5 seconds, 1 second, 2 seconds, 5 seconds, or 10 seconds. The processor 310 sends the location data to the memory 316 along with a time and date stamp indicating when the user 110 was at the location. In some embodiments, the GNSS receiver 312 may be part of a separate GNSS device used by the user 110 for obtaining user directions. In this case, the GNSS receiver 312 transmits data to the building data collection device 104 though a wired connection or a wireless connection, e.g., BLUETOOTH or Wi-Fi.

The seismograph 314 is a device that measures seismic activity. Data collected from a seismograph 314 may include or be used for obtaining safety events or condition of the building. Some or all of these types of data are received or calculated by the processor 310. The processor 310 may collect data at intervals such as every 0.1 seconds, 0.2 seconds, 0.5 seconds, 1 second, 2 seconds, 5 seconds, or 10 seconds and store the data in the memory 316. Each data point is time and date stamped and/or location stamped. In some embodiments, the processor 310 determines intervals between data stored in the memory 316 based on trends in the data.

The OBD port connector 318 is used to collect data from the building computer 302 and/or building telematics sensors 306 via OBD port 304. The OBD port 304 can have a standard interface, such as OBD-I, OBD-1.5, OBD-II, EBD, EBD2, JBD, ADR 79/01, or ADR 79/02. Instead of an OBD port 304, any other port and corresponding connector for receiving data from a building's computer can be used. The building computer 302 may provide information about the building's diagnostics. Building diagnostics data can be used to determine the presence of any building malfunctions, such as poor air quality, seismic events, structural integrity issues, high temperature, loss of electrical power, or fire conditions. With the building diagnostics data, it is possible to determine whether a safety event was caused by the user's actions or related to the malfunction, and thus not reflective of the user's habits. The building may contain additional telematics sensors 306 for, e.g., building tracking, monitoring electrical consumption, and building safety. Data obtained by the building data collection device 104 from the building computer 302 and telematics sensors 306 via the OBD port 304 can supplement or be used instead of data collected by the GNSS receiver 312 and/or seismograph 314. In some embodiments, the building data collection device 104 turns on automatically when the building 102 is with power, and the building 102 may power the building data collection device 104.

In some embodiments, the user data collection device 128 and/or building data collection device 104 may also be configured to communicate with the user 110 via an external user interface, such as a display screen within the building 102. The external user interface includes output components, such as a screen or speakers, and may include input components, such as a touch screen, keyboard, or microphone. The external user interface can output user behavior data, building diagnostics data, a service alert, a malfunction alert, and any data collected from the GNSS receiver 312, seismograph 314, and/or OBD port 304.

In some embodiments, rather than running the data acquisition program on a dedicated data acquisition device installed in the building, the data acquisition program runs on the user's mobile device, such as an IPHONE™, BLACKBERRY™, or any other smartphone or mobile computing device configured to collect data that can be used to analyze user behavior and/or building status. The data can be collected using sensors, such as a GNSS receiver or seismographs, in the mobile device, or the data can be transmitted from the building and received by the mobile device via a wired or wireless connection.

Figure 4:
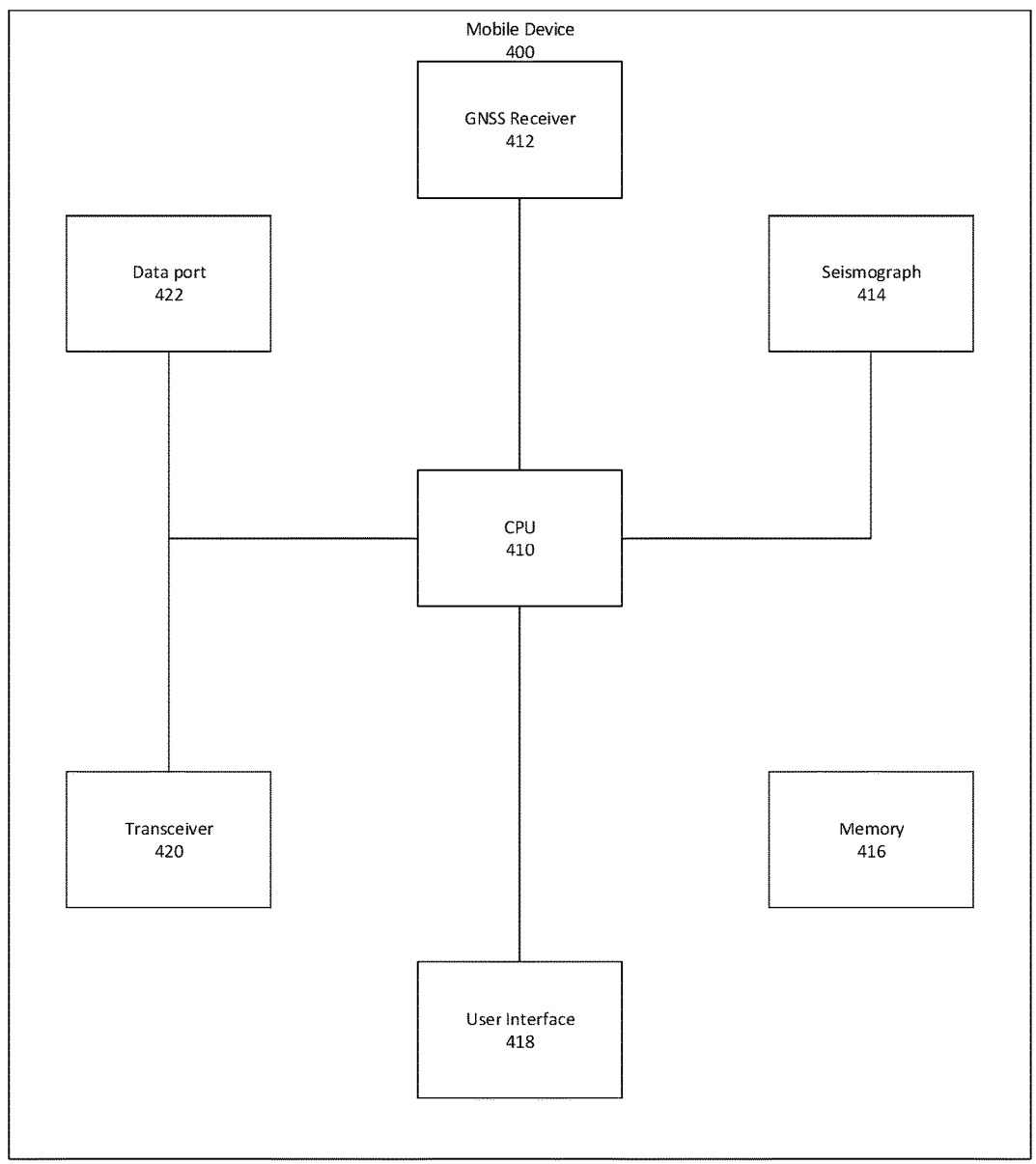
FIG. 4 is a block diagram of a mobile device used within a building or static environment for collecting data used for producing an insurance premium quote, according to an illustrative embodiment of the invention.

FIG. 4 is a block diagram of an exemplary mobile device 400 that can be used instead of the building data collection device 104. The mobile device 400 includes a CPU 410, a GNSS receiver 412, a seismograph 414, and a memory 416, which are similar to the processor 310, the GNSS receiver 312, the seismograph 314, and the memory 316, respectively, described above in relation to FIG. 3. The mobile device 400 also includes a user interface 418, a transceiver 420, and a dataport 422. The CPU 410 is configured to execute a software application for telematics data acquisition. The CPU 410 is in communication with all of the other elements of the mobile device 400 to facilitate the operation of the data collection device 400, and can perform processing similar to the processing performed by the processor 310 described above in relation to FIG. 3.

A user 110 of the mobile device interacts with the mobile device through the user interface 418. The user interface 418 can include one or more of a screen, a touch screen, a speaker, a headphone jack, a keyboard, and a microphone. One or more transceivers 420 are used to connect to and exchange data over a cellular network, the Internet, a BLUETOOTH™ connection, or other wireless communications pathways. The dataport 422 is used for wired communication with the building and/or the telematic monitoring system 130. The data acquisition application can be downloaded from the network or the telematic monitoring system 130 either wirelessly using the transceiver 420 or through a wired connection using the dataport 422. Once the data acquisition application has been installed, it should be executed each time the user 110 enters the building. The user 110 can use the user interface 418 to execute the data acquisition application each time he enters the building. In some embodiments, the mobile device 400 can automatically execute the data acquisition application when the mobile device 400 determines that it is in a building by processing the signals from the GNSS receivers 412 and/or other methods.

In some embodiments, the mobile device 400 is connected to the building by a wireless connection (e.g., BLUETOOTH) or a wired connection using the transceiver 420 or the dataport 422, respectively. In such embodiments, the mobile device 400 can be configured to automatically execute the data acquisition application based on the presence of the building connection. While in the building, the building's computer can send telematics data to the mobile device 400. If the mobile device 400 receives data indicating a building malfunction/safety event, the CPU 410 can create an alert, and the alert can be communicated to the user via the user interface 418. Telematics data received from the building and/or detected by the GNSS receivers 412 or seismographs 414 is stored in memory 416. The telematics data can be sent to the telematic monitoring system 130, building data collection device 104, and/or data processing service 106 in real time, near-real time, or after a longer period of data collection via the transceiver 420, or the data can be transmitted after a period of data collection via the data port 422.

FIG. 5 is a flowchart of a method for providing a building insurance quote using the systems described in relation to FIGS. 1 through 4. The method involves collecting data from the user 110 and building 102 (steps 502 and 504), determining the user's interest in insurance (decision 506), offering temporary coverage (steps 508 through 520), and installing a telematics program to monitor user behavior (steps 522 through 526).

An insurance company collects user telematic data, such as the user's name, address, driver's license number, contact information, payment information, and current insurance information (step 502). Likewise, building telematic data is gather as well (step 504). A decision regarding a user's interest in obtaining insurance is made (decision 506). If interested, user and building telematic data is sent to the insurer (step 508). The types of data transmitted to the insurer for generating a premium price are discussed in greater detail in relation to FIG. 7.

A determination is made whether the user is interested in immediate insurance coverage (decision 510). The user may be interested in immediate coverage if, for example, the purchaser does not currently have an insurance plan or if the purchaser is unsatisfied with his current insurance plan and would like to switch immediately. If the purchaser is interested in immediate coverage, the insurance system 108 determines an initial quote for building insurance based on the user information and building information (step 512). In some embodiments, the insurance system 108 can set this quote to be relatively low to encourage the purchaser to buy the insurance initially. In other embodiments, the insurance system 108 can set the quote relatively high so that if the purchaser receives a long-term rate based on safe driving behavior, the purchaser is encouraged to buy the insurance since the long-term price is lower price than the price they have been paying. The insurance system 108 can use any strategy or calculation for determining the price of the initial quote.

The insurance system 108 sends this initial quote to the user (step 514), and the dealer provides the initial offer to the purchaser (step 516). A decision from the user is made of whether or not he wants to purchase immediate coverage (decision 518). If the purchaser decides to purchase immediate coverage, the insurer processes the billing of the purchaser for the insurance and instructs the insurance system 108 to immediately begin coverage of the user (step 520).

Whether or not the user 110 decided to purchase immediate coverage, the insurer will determine whether the user is interested in receiving a quote for insurance based on the user's driving habits (decision 522). Even if the user was not interested in immediate coverage (decision 510), the insurer will still determine whether the user is interested in receiving a quote for insurance based on the user's driving habits (decision 522). If the user is interested in receiving an insurance quote based on his driving habits, the insurer configures a telematics data acquisition device, for example, by installing the building data collection device 104 described in relation to FIG. 3 that executes the telematics data acquisition program, by installing the telematics data acquisition program for execution on the mobile device 400 described in relation to FIG. 4 (step 524). In other embodiments, the telematics data acquisition program is installed as a program or an add-on to a computing device already in the building. Once the telematics data acquisition program is installed in the building or on a device, the telematics data acquisition program monitors the driving behavior (step 526).

FIG. 6 describes a method for determining an insurance rate for a user based on telematics data once the telematics data acquisition program has been installed. The telematics data acquisition program on the building data collection device 104 or mobile device 400 collects data related to the user's behavior and the condition of the building/building environment, as described in relation to FIGS. 3 and 4 (step 602), during a data acquisition period or monitoring period. The user 110 can be monitored for any period of time over which a sufficient amount of data to analyze the user's user behavior can be collected, e.g., 1 month, 2 months, 3 months, or 6 months.

As the data is being collected or after the data has been collected, the building data collection device 104 or mobile device 400 transmits the data to the insurance system 108 (step 604). As previously mentioned, the data may be processed by the telematic monitoring system 130 and/or a third party data processing service 106 before being sent to the insurance system 108. The insurance system 108 then determines a quote for the insurance (step 606) based on the received telematics data as well as data related to the building and the user 110. Determining the quote for insurance is described in further detail in relation to FIG. 7.

Once the quote has been determined, the insurance system 108 transmits the insurance quote to the user 110 for his consideration (step 610). The quote may include several possible types of coverage at different prices from which the user 110 can choose. If the agent cannot provide the quote to the user 110 in person, the agent or the insurance company can contact the user 110 and provide the quote by telephone, mail, electronic mail, or any other communications means.

The user 110 then determines whether to purchase coverage at the offered price (step 612). If the user 110 agrees to purchase insurance coverage based on the quote, the insurance company provides coverage and proof of insurance to the user 110 (step 614). If the user 110 declines coverage, the insurance company may provide periodic reminders about the rate and any promotions available (step 616). If the user 110 declined the insurance because his health status or building/building environmental factors drove the price too high, the user 110 may be given the option to improve his health and/or user behavior with continued monitoring. In this case, if the user 110 later decides to purchase insurance because his health and/or user improved and his rate was reduced, the insurance company may request that the user 110 is continually monitored to ensure that the user 110 continues acting safely. If the user 110 declined the insurance for other reasons, he can still agree to continual monitoring in return for various incentives, including, for example, a continued agreement to pay for the users deductible if needed. The insurance company can continue to provide updated insurance quotes, e.g., on the receipts for services received. This also provides additional telematics data for the insurance company to use in generating quotes for the user 110 and other prospective customers.

FIG. 7 provides greater detail into the factors involved in developing an insurance quote. The insurance quote is derived from four main classes of data: building data 710, user data 720, user telematic data 770, and building telematics data 730. The building telematics data 730 is processed to generate data related to user behavior and building/building environmental conditions. Based on the building condition, a malfunction/safety alert may be provided to the user 110. In addition to the building data 710, user data 720, user telematic data 770, and telematics data 730, data from previous telematics monitoring 762 and service history data 760 can be used to determine the insurance quote 780. The processing steps for processing the data described in relation to FIG. 7 and calculating insurance rates can be performed at the insurance system 108, the third party data processing service 106, the telematic monitoring system 130, the building data collection device 104 or mobile device 400, or any combination of these systems and devices.

Building data 710 is comprised of data relating to the building. The building data 710 includes construction materials, building location, nature of building use (commercial, industrial, etc.), age of building, etc. If the building has special feature, this data is also included in the building data 710. The building data 710 also includes the age of the building 711, the construction materials of the building 712, and the history of the building 713. The history 713 includes information on any events such as accidents or safety events, of the building or those in the area. The history 713 also includes any available service records and any available information related to how the building was used by its previous owner(s). The building data may also include the purchase price and/or resale price of the building.

User data 720 is comprised of the data associated with the user 110. The user 112 data 720 includes basic contact information of the user 721, including the user's name, address, telephone number(s), fax number, email address, etc. The user data 720 also includes basic demographic data, such as gender 722 and age 723. The user data 720 also includes data that can be used to analyze the user's finances and financial responsibility, such as social security number 724 and employment information 725. The user data 720 also includes the user's medical history 726, with which the insurance company 108 can retrieve information on the user's user history.

The user telematics data 770 includes data collected by the data acquisition program. The user telematic data includes sensed data about the user's health and overall condition such as, blood pressure, body temperature, perspiration, body mass index, blood glucose level, blood alcohol content, brain function, activity level, respiratory rate, eye dilatation, etc. Additionally, or alternatively the user telematic data includes sensed data about the user's environment. Such data includes, but is not limited to, oxygen content, carbon monoxide level, methane gas detection, hydrogen sulfide gas presence, the presence of any dangerous or potentially harmful fluids or gasses, etc. The user telematic data 770 is generally a measure of any health/environmental factor the user 110 is experiencing during or around building operation.

The building telematics data 730 includes data collected by the data acquisition program. The building telematics data 730 includes GNSS data 731 and seismograph data 732 collected by the GNSS receivers 312 or 412 and seismographs 314 or 414, respectively. The telematics data also includes data collected from the OBD port, such as energy usage data 733, safety event deployment data 734, and HVAC diagnostics data 735. The telematics data 730, particularly the GNSS data 731, seismograph data 732, and any data received from the building computer relating to safety events (e.g., fire event, carbon dioxide event, etc.) are processed to generate metrics indicative of user 110 behavior.

The building telematics data 730 is also analyzed to determine whether the building is malfunctioning or has experienced a safety event (decisions 750 and 752). The building diagnostics data 735, the air quality data 735, and data indicating the misuse are particularly relevant for these determinations. If the building is malfunctioning or has experienced a safety event, an alert (754 or 756) is generated and communicated to the user's telephone, smart phone, computer, or any other communications device, or to the building 102. The alert can be in the form of a phone call, a voice mail, a text message, an email, an alert on the building's dashboard, or any other type of communication. The alert can include the type of safety event or a description of the malfunction, a level of urgency of reacting to the safety event or correcting the malfunction.

In some embodiments, the user 110 may have telematics data 762 from previous telematics monitoring that was performed by the same insurance company, a different insurance company, or not associated with an insurance company. The previous telematics data 762 may be similar to the telematics data 730. If the insurance system 108 can access the previous telematics data 762, it can use this to generate an insurance quote without collecting telematics data 730. In this case, a quote can be generated as soon as the previous telematics data 762 is available to the insurance system 108. In other embodiments, telematics data 730 is still gathered, and it is supplemented by the previous telematics data 762. If the telematics data 762 was collected by a different insurance company or a different building data collection device 104, the format of the data may not be in the format used by the insurance system 108 for calculating an insurance premium. In this case, the insurance system 108 can convert the data format into the data format output by the insurance company's data acquisition program.

In some embodiments, data from a third party data provider 764 is also accessed for generating the insurance quote. For example, data from a third party data provider 132 may provide additional information related to the user 110, such as the user's safety record or credit history. Other third party data, such as injury accidents and weather data, is processed in conjunction with the received telematics data to evaluate user patterns in view of the road conditions, and may be used when evaluating the user.

If the user 110 already has an insurance plan, the user 110 may provide current insurance data 770 related to his current insurance plan. The user 110 can provide a summary of coverages provided 771, the premium price of the plan 772, and the deductible price of the plan 773, which the insurance company can use to determine a competitive quote. The user 110 can also provide the renewal date 774. Before the renewal date 774, the insurance company can provide reminders or advertisements to the user 110 to remind him of his rate and promotions. The current insurance data 770 also can include information on any claims filed on the insurance plan 775, which can be used to supplement the user's safety record and to evaluate the insurance risk of the user 110.

Based on some or all of the building data 710, user 110 data 720, user telematic data 790, building telematics data 730, processed user behavior characteristics 740-748, service history 760, previous telematics data 762, third party data 764, and current insurance data 770, the insurance system 108 or an underwriter determines a premium price or set of premium prices based on coverage for the user 110. Safe user 110 behaviors, user health factors within tolerance, user environmental factors within tolerance, good building conditions, and good financial history may be associated with lower insurance premiums. The various factors may be rated separately, e.g., an overall safety rating can be calculated, or a user 110 behavior rating can be calculated. The factors can be weighted and the premium price based on the various rating factors and their relative weights. In some embodiments, the insurance system 108 or an underwriter uses the telematics data 730 in an algorithm for generating an insurance quote. In other embodiments, the insurance system 108 or an underwriter uses the telematics data 730 to calculate a discount to apply to an insurance quote that is determined by the insurance system 108 or an underwriter without the telematics data 130. In some embodiments, some of the data, particularly the telematics data, is used to determine whether an eligibility requirement is satisfied. For example, if the telematics data shows that the user's safety behaviors or health issues are too unsafe, the insurance company may decide not to offer insurance to the user 110. If the telematics data meets the eligibility requirement, the telematics data may or may not be used further in calculating the insurance quote 780.

In some embodiments, the insurance quote 780 is not based on the telematics data but merely the fact that telematics data is being collected. For example, the insurance company can give the user 110 a discount on an insurance premium if the insurance company knows that telematics data is being collected, but the insurance company may not use the telematics data itself for pricing the insurance plan. The providing of an incentive can be similarly based on whether or not telematics data is being collected. In some embodiments, the insurance quote 780 and/or the incentive is based on the frequency or duration of the telematics data collection. Alternatively, the incentive or discount can be based on the frequency or duration with which the user 110 runs the telematics data acquisition program.

An aspect of the disclosure includes a system for processing environmental safety status, health data, and building data related to determination of an insurance quote for a user. The system comprising a communications interface configured to receive health telematics data collected by a telematics data acquisition device. The telematics data acquisition device is configured to collect health telematic data of a building environmental safety status. The health telematic data being indicative of the building environmental safety status health while within a building. The system is configured to receive building telematic data collected by a telematics data acquisition device. The telematics data acquisition device is configured to collect telematics data of a building. The telematics data is indicative of the safety of the building. The system is configured to provide the health telematic and the building telematic data to a business logic processor for the development of a insurance quote based on at least one of the received health telematics data or building telematic data. The system is configured to transmit the insurance quote to the user.

A further aspect includes the insurance quote system disclosed includes the health telematics data collected by a telematics data acquisition device. The data contains telematic data that is at least one of a data related to building/user environment structural condition, building/user environment air quality, geographic location, temperature/humidity level, HVAC status, security devices, ingress/egress configuration, building materials, nature of use (current/historic) and surrounding environmental conditions.

A further aspect includes the insurance quote system wherein health telematics data indicates an unsafe condition for the user.

Yet another aspect includes an insurance quote system wherein the telematics data indicative of safety of the building includes telematic data that is at least one of a oxygen content, carbon monoxide level, methane gas detection, hydrogen sulfide gas, or dangerous or poisonous fluid presence.

A further aspect includes an insurance quote system wherein health telematics data indicates an unsafe condition for the user.

Another aspect includes an insurance quote system further comprising transmitting the insurance quote to an insurance agent or insurance company.

A still further aspect includes one or more tangible computer readable media storing computer readable instructions that, when executed, perform a method of providing a insurance quote to a user based upon human health telematic data and building telematic data, including receiving health telematic data via a communications interface health telematics data collected by a telematics data acquisition device. Also, receiving building telematic data via a communications interface building telematics data collected by a telematics data acquisition device. This includes determining an insurance quote based on the received health telematic data and the received building telematic data. Also included is transmitting the insurance quote to the user.

The computer readable media includes the step of receiving health telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Also included is the computer readable media wherein the health telematic data indicates the user is in an unsafe condition.

Additionally included is the computer readable media wherein the step of receiving building telematic data includes receiving building telematic data of at least one of a data related to building/user environment structural condition, building/user environment air quality, geographic location, temperature/humidity level, HVAC status, security devices, ingress/egress configuration, building materials, nature of use (current/historic) and surrounding environmental conditions.

The computer readable media wherein the building telematic data indicates the user is in or near an unsafe environment or location.

Also included is the computer readable media wherein the step of transmitting the insurance quote to the user includes transmitting the insurance quote based upon an unsafe condition detected with the user's health.

Further, the computer readable media wherein the unsafe condition detected with the user's health is related to user telematic data. This includes data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

An additional aspect includes the computer readable media wherein the step of transmitting the insurance quote to the user includes transmitting the hazard alarm/notification based upon an unsafe condition detected with environmental conditions in the user's location.

Also included is the computer readable media wherein the environmental conditions include at least one of a data related to building/user environment structural condition, building/user environment air quality, geographic location, temperature/humidity level, HVAC status, security devices, ingress/egress configuration, building materials, nature of use (current/historic) and surrounding environmental conditions.

Yet another non limiting aspect of this disclosure includes a sensor system that has a first sensor, to be worn by a user. The first sensor outputting a first sensor data indicative of measured at least one user health telematic data. Additionally included is a second sensor, in communication with a building being occupied by the user, the second sensor outputting a second sensor data indicative of a measured at least one building telematic data. Also, a computing unit, in communication with the first sensor and the second sensor. The computing unit storing program instructions for execution by the computing unit to receive the first sensor data and the second sensor data, calculate a risk level associated with the first sensor data and the second sensor data, and output a insurance quote feedback signal to the user indicative of the risk level of the first sensor data and the second sensor data.

Also included is a sensor system wherein the first sensor data is user telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Also included is a sensor system wherein the output signal to the user is a insurance quote indicative of the user telematic data indicating the user spending excessive time in an area having a predetermined dangerous or unsafe level or condition.

Another aspect includes a sensor system further including providing an insurance quote output feedback signal to an insurance company or insurance agent.

Yet another aspect includes a sensor system wherein the second sensor data is data related to building/user environment structural condition, building/user environment air quality, geographic location, temperature/humidity level, HVAC status, security devices, ingress/egress configuration, building materials, nature of use (current/historic) and surrounding environmental conditions.

Also, a sensor system further including providing an insurance quote output feedback signal to an insurance company or an insurance agent.

Another aspect of the disclosure is a method for providing an insurance quote based upon human health telematic data and building telematic data. The method comprising receiving, by a communications interface, health telematics data collected by a telematics data acquisition device, the health telematics data being indicative of a building environmental safety status health while within a building. Also, receiving, by a communications interface, building telematic data collected by a telematics data acquisition device, the building telematics data being indicative of a building environmental safety status health while within a building. Further, determining, by the business logic processor, a insurance quote for the user based on the received health telematic data and building telematic data. Additionally, providing by the business logic processor the insurance quote to the communications interface. Also, transmitting, by the communications interface, the insurance quote to the user.

The method further comprising transmitting, by the communications interface, the insurance quote to an insurance company or an insurance agent.

A further aspect of the disclosure is a method of providing human telematic based insurance quote to a user based upon human telematic data and building telematic data. The additional aspect comprising providing a first sensor, to be worn by a user, a first sensor data indicative of measured at least one user health telematic data. Also, providing a second sensor, in communication with a building being occupied by the user, the second sensor outputting a second sensor data indicative of a measured at least one building telematic data. This aspect also includes providing a computing unit, in communication with the first sensor and the second sensor, the computing unit storing program instructions for execution by the computing unit. The computing unit receiving the first sensor data and the second sensor data and calculating a risk level associated with the first sensor data and the second sensor data. The computing unit is also providing an insurance quote output feedback signal indicative of the risk level of first sensor data and the second sensor data to the user.

The method further comprising transmitting, by the communications interface, the insurance quote to an insurance company or an insurance agent.

An additional aspect includes a method wherein the user health telematic data is user telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Yet another aspect includes a method wherein the building telematic data include at least one of a data related to building/user environment structural condition, building/user environment air quality, geographic location, temperature/humidity level, HVAC status, security devices, ingress/egress configuration, building materials, nature of use (current/historic) and surrounding environmental conditions.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for processing health telematic data and building telematic data related to the determination of an insurance quote provided to a user using a non-transitory computer-readable storage medium with instructions stored thereon that, when executed, direct a processor to perform acts comprising:
   sensing a health telematic data via a wearable telematics data acquisition device worn by a user that provides substantially continuous health telematic data status monitoring, wherein the health telematic data relates to at least one user health condition data;
   receiving the health telematic data via a communications interface, health telematics data collected by the wearable telematics data acquisition device;
   receiving building telematic data via the communications interface, building telematics data collected by a building telematics data acquisition device, the building telematic data being indicative of historic building data and the historical nature of prior building use;
   determining an insurance quote based on the received health telematic data and the received building telematic data, and,
   transmitting the insurance quote to the user via a mobile device for immediate acceptance.

2. The method of claim 1, wherein the step of receiving health telematic data includes user health condition data including at least one of a body mass index, blood pressure, respiratory rate, heart rate, perspiration, body temperature, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

3. The method of claim 2, wherein the health telematic data indicates the user is in an unsafe condition.

4. The method of claim 3, wherein the unsafe condition detected with the user's health is related to user telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

5. The method of claim 1, wherein the step of receiving building telematic data includes receiving building telematic data of at least one of a data related to building/user environment structural condition, building/user environment air quality, geographic location, temperature/humidity level, HVAC status, security devices, ingress/egress configuration, building materials, nature of use (current/historic) and surrounding environmental conditions.

6. The method of claim 5, wherein the building telematic data indicates the user is in or near an unsafe environment or location.

7. The method of claim 1, further comprising, transmitting the insurance quote to an insurance company.

8. The method of claim 1, wherein the building telematic data is current building telematic data.

9. The method of claim 1, wherein the building telematic data is historic building telematic data.

10. The method of claim 1, wherein the building telematic data includes both current building telematic data and historic telematic data.

11. The method of claim 1, wherein acceptance of the insurance quote yields a binding insurance policy.

12. The method of claim 11, wherein the binding policy covers either personal or real property.

13. A method to perform acts comprising:
   providing a first sensor, the first sensor being a wearable device configured to substantially continually sense a health telematic data while the user is within a building, the first sensor providing data indicative of measured at least one user health telematic data relating to at least one of a body mass index, blood pressure, respiratory rate, heart rate, perspiration, body temperature, blood sugar level, brain function (EEG), vacillations in blood sugar level, hours of sleep, physical activity rate and duration, water consumption, food consumption, alcohol consumption, amount of sunlight exposure, and/or exposure to air or water pollutants;
   providing a second sensor, in communication with a building being occupied by the user, the second sensor outputting a second sensor data indicative of a at least one historic building telematic data including data of prior building use;

providing a computing unit, in communication with the first sensor and the second sensor, the computing unit storing program instructions for execution by the computing unit to:

receive the first sensor data and the second sensor data;

calculate a risk level associated with the first sensor data and the second sensor data;

determine an insurance quote based on the risk level; and, transmit the insurance quote to the user via a mobile device for immediate acceptance.

14. The method of claim 13, further comprising transmitting the insurance quote to the user via email.

15. The method of claim 13, wherein at least one historic building telematic data includes at least one of a structural condition, building materials, and nature of use.

16. The method of claim 15, wherein the at least one historic building telematic data indicates the historical nature of the building may cause an unsafe environment.

17. A method performed using a tangible computer-readable storage medium with instructions stored thereon that, when executed, direct a processor to perform the method comprising:

receiving a user health telematic data collected substantially continuously, the health telematic data being indicative of a user's current health status while within a building;

receiving a user environmental telematic data indicative of an environmental quality around the user;

receiving a historic building telematic data indicative of historical building data and the historical nature of prior building use;

calculating a risk level associated with the received user health telematic data, user environmental telematic data, and the historic building telematic data; and, calculating an insurance quote indicative of the risk level based upon the user health telematic data, user environmental telematic data, and the historic building telematic data, and;

transmitting the insurance quote to the user via a mobile device for immediate acceptance.

18. The method of claim 17, further comprising transmitting the insurance quote to an insurance company or insurance agent.

19. The method of claim 17, wherein historic building telematic data indicates that a building has endured a seismic event.

20. The method of claim 17, wherein the building telematic data include at least one of a data related to building/user environment structural condition, building/user environment air quality, geographic location, temperature/humidity level, HVAC status, security devices, ingress/egress configuration, building materials, nature of use (current/historic) and surrounding environmental conditions.

* * * * *